(12) United States Patent
Romaine

(10) Patent No.: US 8,597,628 B2
(45) Date of Patent: Dec. 3, 2013

(54) COSMETIC WATER-IN-OIL EMULSION COMPOSITIONS

(75) Inventor: Carolyn Romaine, Somerset, NJ (US)

(73) Assignee: Chanel Parfums Beaute, Neuilly sur Seine (FR)

( * ) Notice: Subject to any disclaimer, the term of this patent is extended or adjusted under 35 U.S.C. 154(b) by 357 days.

(21) Appl. No.: 12/920,538

(22) PCT Filed: Mar. 10, 2009

(86) PCT No.: PCT/EP2009/052791
§ 371 (c)(1),
(2), (4) Date: Sep. 1, 2010

(87) PCT Pub. No.: WO2009/112492
PCT Pub. Date: Sep. 17, 2009

(65) Prior Publication Data
US 2011/0014138 A1    Jan. 20, 2011

Related U.S. Application Data

(60) Provisional application No. 61/035,095, filed on Mar. 10, 2008.

(51) Int. Cl.
*A61K 8/00* (2006.01)
*A61K 8/06* (2006.01)
*A61K 8/25* (2006.01)
*A61K 8/89* (2006.01)

(52) U.S. Cl.
USPC ........ 424/78.02; 424/78.03; 424/69; 424/401

(58) Field of Classification Search
USPC .............................. 424/78.02, 78.03, 69, 401
See application file for complete search history.

(56) References Cited

U.S. PATENT DOCUMENTS

| 4,980,167 A | 12/1990 | Harashima et al. |
| 5,538,793 A | 7/1996 | Inokuchi et al. |
| 6,284,281 B1 | 9/2001 | Chevalier et al. |
| 2002/0012643 A1* | 1/2002 | Ramin et al. ................. 424/401 |
| 2002/0182158 A1 | 12/2002 | Christophides-Lordi et al. |
| 2004/0265348 A1 | 12/2004 | Hollenberg et al. |
| 2006/0239942 A1 | 10/2006 | Shah et al. |
| 2008/0038299 A1* | 2/2008 | Strodtholz et al. ............ 424/401 |

FOREIGN PATENT DOCUMENTS

| EP | 1103245 A1 | 5/2001 |
| FR | 2816506 A1 | 5/2002 |
| WO | 0072817 A1 | 12/2000 |
| WO | 2007008458 A1 | 1/2007 |

OTHER PUBLICATIONS

International Search Report, dated Feb. 25, 2010, from corresponding PCT application.
"Evian Brumisateur Facial Spray", Evian Product Information, Feb. 9, 2008, (1 page), Cited in International Search Report.

* cited by examiner

*Primary Examiner* — Mina Haghighatian
(74) *Attorney, Agent, or Firm* — Young & Thompson

(57) ABSTRACT

Cosmetic water-in-oil emulsion compositions containing solid particles and high concentrations of a specific silicone elastomer and including high content of polysilicon-11, solid particles providing at least one optical effect, and at least one silicon emulsifier are suitable for use for making up the face and/or lips or eyelids, preferably as foundations. They may also be used to as a base for make-up, or as a skin care cream to be applied on the body or face. These compositions result in a product that enhances the overall appearance of the skin by providing strong blurring effects to give anti-wrinkle/fine line effects, skin smoothness, and radiance while unifying color complexion. These compositions also have unique sensorial properties.

19 Claims, No Drawings

COSMETIC WATER-IN-OIL EMULSION COMPOSITIONS

The present invention relates to cosmetic water-in-oil emulsion compositions containing solid particles, and high concentrations of a specific silicone elastomer, mainly aimed at providing a uniform coverage on the skin.

Cosmetic products developed with the aim of masking imperfections of the skin, either unify the colour complexion or give the skin a smoother appearance or a radiant healthy glow, and contain solid particles having an optical effect on the skin to achieve that purpose.

In general, to provide a uniform coverage on the skin a minimum amount of pigments is necessary in the composition. Thus, foundations which unify the colour complexion generally contain high amounts of pigments or white fillers.

Recently cosmetic products have been developed to have facial sculpting or "morphing" properties where the visual contrast between the shadowed (the sides of the face for example) and highlighted areas (the forehead, cheekbones and chin for example) on the skin is accentuated (example of sculpting foundation). Different types of cosmetic ingredients are known to provide these various optical effects.

Moreover, it is known that inclusion of powders with high diffuse reflectance, low specular reflectance and high diffuse transmittance otherwise known as soft-focus powders or blurring agents give the skin a smoother appearance, by reducing the difference in luminosity between the valley and the edges of wrinkles and imperfections.

Skin mattifying powders can also be used mainly to reduce the shininess of skin by adsorbing sebum and the excess oil of the composition not adsorbed by the skin.

Furthermore, as well as having certain optical effects it is desirable that the cosmetic product developed with the aim of masking imperfections of the skin has a soft, silky, powdery and non-greasy touch.

The use of silicone elastomers in cosmetic products for the specific purpose of enhancing the overall appearance of skin is well known especially for the effects of blurring wrinkle lines, smoothing the skin, giving a unified complexion and mattifying. Furthermore the use of these polymers in cosmetic products for their pleasing aesthetic properties is also well known in the art.

Since the beginning of the 1990s a smooth, powdery feel in formulations has been often achieved using organopolysiloxane cross-polymers also commonly known as silicone elastomers.

It is very desirable to be able to deliver high levels of silicone elastomers in a cosmetic composition. It is also desirable to deliver the silicone elastomer in the form of an emulsion to the end user as these types of vehicles help provide very sensorially and aesthetically pleasing attributes. Generally speaking, oil-in-water type emulsions are more desirable than water-in-oil types as water-in-oil types are generally associated with having a greasy feel on the skin.

One of the problems associated with water in oil emulsions containing pigments or other solid particles with an optical effect such as soft focus powders, is also that these solid particles need to be dispersed so that the emulsion be stable. For example U.S. Pat. No. 5,599,533 describes the use of electrolytes, high amount of surfactants, polyols and hydrocolloids, to stabilise water-in-oil emulsions containing silicon elastomers.

Emulsions with a significant percentage of stabilisers, albeit stable, have the disadvantage of limiting the further capacity in the formula to accept additional components which can provide, for example, good skin feel or touch.

Thus, there exists a need to provide stable water-in-oil emulsions, containing solid particles having an optical effect, and that also have an improved powdery, smooth, non-sticky feel.

The present inventors have carried out a series of experiments to overcome the above mentioned problems. They have succeeded in providing a stable water-in-oil emulsion that provides the desired optical result (by unifying the complexion, giving a smooth appearance to the skin) while maintaining a silky non-greasy feel. Moreover, the make-up cosmetic compositions of the invention unexpectedly give the skin a radiant glow. In particular they have discovered that the inclusion of a minimum quantity of a particular silicone elastomer gives rise to stable emulsions, even in the presence of high percentages of pigments and without the need of a significant percentage of stabilisers.

The invention described here within covers in particular make-up compositions. It is desirable to have a make-up composition that in addition to providing color to the skin, also provides enhanced overall skin appearance. To accomplish this, it is typical to have a very detectable/high coverage foundation to hide the imperfections. The present invention provides a way to deliver the benefits of improving overall appearance without having a very high coverage make-up but in fact, a non-detectable/natural finish.

These compositions result in a product that enhances the overall appearance of the skin by providing strong blurring effects to give anti-wrinkle/fine line effects, skin smoothness, and radiance while unifying color complexion. These compositions also have unique sensorial properties as shown hereafter.

The present invention also provides a method for the manufacture of these water-in-oil emulsions.

One of the inconveniences of most make-up compositions is that after a number of hours after application on the skin they may start to look and/or feel dry. A method for refreshing the cosmetic composition comprising the emulsion of the invention is thus herein provided. A further aspect of the invention is a kit which facilitates the utilization of the said method.

SUMMARY OF THE INVENTION

The present invention deals with a water-in-oil emulsion comprising a high content of polysilicone-11 as a silicon elastomer, solid particles providing at least one optical effect, and at least one silicon emulsifier.

The emulsions of the invention are suitable for use for making up the face and/or lips or eyelids, preferably as foundations. They may also be used as a skin care cream to be applied on the body or face. They may be in the form of a liquid, cream, gel or semi-solid.

This water-in-oil emulsion contains a significant proportion of polysilicone-11. The present inventors have surprisingly found that this specific elastomer can lead to stable water-in-oil emulsions without containing high proportions of stabilizers. The content of polysilicon-11 is preferably higher than the content of silicon emulsifier.

According one embodiment, the present invention pertains to a water-in-oil emulsion comprising:
(a) at least 5 wt. % poly silicone-11 based on the total weight of the composition, in the form of a gel with a hydrophobic solvent,
(b) at least 0.5 wt. % of solid particles having an optical effect based on the total weight of the composition, and (c) at least one silicone emulsifier chosen from a dimethicone copolyol comprising at least one oxyethylene group and at least one oxypropylene group.

As a preferred embodiment, the hydrophobic solvent comprises at least one volatile solvent.

As another preferred embodiment, the hydrophobic solvent is volatile.

The present invention also provides a process for preparing said emulsion comprising the following steps:
1—Dispersion of the Polysilicone-11 in the hydrophobic solvent to form a gel,
2—Addition of the silicone emulsifier to the previous gel, and mixture with a water phase,
3—Addition of the solid particles providing at least one optical effect.

The invention also provides a process for making up skin and/or lips and/or for protecting skin against UV damage.

Another aspect of the invention is a method for applying and refreshing make-up comprising the steps of
1—Applying a cosmetic composition comprising the emulsion of the invention to the skin;
2—After an interval of time ranging from 2 to 12 hours applying a second composition which can be water or an aqueous composition, or a non-silicon oil or a non-silicon oil-based composition onto the layer of the previously applied first cosmetic composition;
3—Blending the second composition into the first.

Another aspect of the invention is a kit-of-parts that facilitates the application of the above method. The kit is comprised of containers that serve as reservoirs for the first and second compositions of the method above.

According to a preferred embodiment, the present invention is a water-in-oil ("w/o") emulsion comprising at least 5 wt % of the silicone elastomer polysilicone-11, and at least 0.5 wt % solid particles providing at least one optical effect, and also at least one silicon emulsifier. The compositions of the invention are stable as demonstrated in the examples section.

Polysilicone-11:

An essential component of the invention is the silicone elastomer with the International Nomenclature of Cosmetic Ingredients (INCI) name Polysilicone-11. The exclusive properties of this particular elastomer provide the inventive compositions with unique aesthetic and performance benefits, as well as emulsion stability.

Polysilicon-11 is preferably present in an amount of about 6 to about 30 wt %, more preferably from about 6 to about 12 wt % based on the weight of the composition.

Polysilicone-11 is the reaction product of —Si-H containing polysiloxane with an alpha,omega-vinyldimethicone, in the presence of a platinum catalyst and a solvent which may be any one of vegetable oils (such as jojoba or castor), paraffin, petrolatum, hydrogenated polyisobutene, and mineral oil. The solvent content of the resultant gel can range from 85 to 96 wt %, and the viscosity is generally greater than 200 cSt at 25° C. The —Si—H containing polysiloxane is added to the solvent and then is crosslinked by the addition of the catalyst and alpha,omega-vinyldimethicone. Standard reaction conditions known in the art for hydrosilylation via solvent process may be used.

The —Si—H containing polysiloxane can be represented by compounds of formulas:

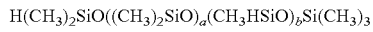
$H(CH_3)_2SiO((CH_3)_2SiO)_a(CH_3HSiO)_bSi(CH_3)_3$

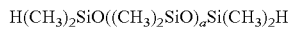
$H(CH_3)_2SiO((CH_3)_2SiO)_aSi(CH_3)_2H$

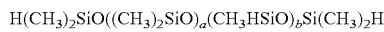
$H(CH_3)_2SiO((CH_3)_2SiO)_a(CH_3HSiO)_bSi(CH_3)_2H$ where a is 1-250 and b is 1-250.

The platinum catalyst may be represented by hexachloroplatinic acid in a solvent, or a platinum complex of $Pt_2[(CH_2=CH)Me_2Si]_2O$.

Polysilicon-11 is used in this invention in the form of a gel in a hydrophobic solvent. Polysilicon-11 can be mixed into said hydrophobic solvent to form a gel, prior addition to the other ingredients of the composition.

Polysilicone-11 may be dispersed in the hydrophobic solvent, rather than solubilized therein. Nevertheless, this component is referred to as a "solvent". The solvents used may be volatile or non-volatile, or a mixture of volatile and non-volatile and are liquid at room temperature. In this context, the term "volatile hydrophobic solvent" means that the solvent exhibits a significant vapor pressure at ambient conditions (e.g., 1 atmosphere at 25° C.), as understood by those skilled in the scientific arts. Specially, the solvent has a boiling point at one atmosphere of about 260° C. or less, preferably about 230° C. or less, more preferably about 215° C. or less, and most preferably about 210° C.

Those skilled in the art are familiar with the solvents normally used in cosmetic applications. Examples of hydrophobic solvents presented for illustration purposes are linear silicones or cyclic silicones as well as hydrocarbons, which can be linear or branched, saturated or unsaturated, hydrogenated or not, alkoxylated or not, or mixtures thereof.

Non-volatile hydrophobic solvents which are suitable for use in the present compositions include, but are not limited to esters such as mono-, di-, and triesters and in general polyesters made by reacting mono-, di-, and tri- and in general polyols with mono-, di-, tri- and in general polycarboxylic acids, which may be linear or branched, with any or no degree of unsaturatation, aliphatic or aromatic in any of the chains, alkoxylated or not, and their mixtures. This includes esters from mono- or polyglyceryl derivatives. Included are natural oils, fats, and esters.

Non-volatile hydrophobic solvents suitable for use in the present compositions also include non-volatile polysiloxanes.

Examples of non-volatile hydrophobic solvents include, but are not limited to, isononyl isononanoate, dimethicone, phenyltrimethicone, and mixtures thereof.

Volatile hydrophobic solvents which are suitable for use in the present compositions include, but are not limited to, volatile silicones, branched chain hydrocarbons, and mixtures thereof. Preferred silicones useful as the volatile hydrophobic solvent include, but are not limited to, volatile siloxanes such as low molecular weight polydimethylsiloxane (dimethicone) of viscosity below 6 cStat 25° C., phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane, and mixtures thereof. More preferred among the volatile silicones are cyclomethicones, examples of which include octamethyl cyclotetrasiloxane and decamethyl cyclopentasiloxane, which are commonly referred to as D4 and D5 cyclomethicone, respectively.

Additional examples of preferred volatile silicones, include, but are not limited to, cyclopentasiloxane (commercially available from Momentive as SF™ 1202), hexylmethicone (commercially available from Archimica as SILCARE™ 41M10), caprylyl methicone (commercially available from Archimica as sSILCARE™ 41M15), stearoxytrimethylsilane, methyl trimethicone (commercially available from Shin-Etsu Chemical, Japan as TMF 1.5™) and mixtures thereof.

Hydrophobic branched chain hydrocarbons useful as the volatile, hydrophobic solvent herein include, but are not limited to, those containing from about 7 to about 14, more preferably from about 10 to about 13, and most preferably from about 11 to about 12 carbon atoms. Saturated hydrocarbons are preferred, although it is not intended to exclude unsaturated hydrocarbons. Examples of such preferred branched chain hydrocarbons include isoparaffins of the above chain sizes and hydrogenated polyisobutene. Specific examples of isoparaffins include ISOPAR™ E (C8-C9 isoparaffins), ISOPAR™ H and K (C11-C12 isoparaffins), and ISOPAR™ L (C11-C13 isoparaffins) or mixtures thereof (all commercially available from Exxon Chemical Co.) Other suitable branched chain hydrocarbons are isododecane, isoundecane and isohexadecane. Specific examples of hydrogenated polyisobutene include DEDRAFLOW® 5 commercially available from Cosmo Chem.

Isododecane is preferred and is commercially available from Presperse, Inc. as PERMETHYL™ 99A.

The water-in-oil emulsion compositions typically comprise the hydrophobic solvent in an amount suitable to form a continuous phase with the silicone emulsifier.

In one embodiment, the emulsion composition comprises from about 5 wt % to about 35 wt %, more preferably from about 8 wt % to about 25 wt %, even more preferably from about 10 wt % to about 20 wt %, of the hydrophobic solvent, based on the weight of the composition.

Polysilicon-11 is commercially available as a range of gels from Grant Industries, Elmwood Park N.J., U.S.A. under the trade name GRANSIL®. The gels in this commercial range differ from each other in elastomer concentration, viscosity and solvent type:

TABLE 1

| | Trade name |
|---|---|
| Volatile Hydrophobic Solvent | |
| Cyclotetrasiloxane | GRANSIL GCM ® |
| Cyclopentasiloxane | GRANSIL GCM-5 ® |
| Cyclopentasiloxane | GRANSIL RPS ® |
| Cyclopentasiloxane | GI CD-10 ™ |
| Isododecane and Cyclotetrasiloxane | GRANSIL IDS ® |
| Isododecane and Cyclopentasiloxane | GRANSIL IDS-5 ® |
| Isododecane | GRANSIL PC-12 ® |
| Dimethicone (5 cst) | GRANSIL DM5 ® |
| Cyclotetrasiloxane and Dimethicone (5 cst) | GRANSIL DMCM ® |
| Cyclopentasiloxane and Dimethicone (5 cst) | GRANSIL DMCM-5 ® |
| Dimethicone (6 cst) | GRANSIL DMG-6 ® |
| Non-Volatile Hydrophobic Solvent | |
| Isononyl Isononanoate | GRANSIL ININ ® |
| Dimethicone (20 cst) | GRANSIL DMG-20 ® |
| Phenyltrimethicone | GRANSIL PM ® |
| Mixture of Volatile and Non Volatile Hydrophobic Solvent | |
| Dimethicone and Isododecane | GRANSIL DMID ® |

Other gels suitable for the present composition according to the invention are:

GRANSIL WO®
INCI: Cyclopentasiloxane (and) Polysilicone-11 (and) Glyceryl Laurate (and) Cetyl PEG/PPG 10/1 Dimethicone (and) PEG/PPG-18/18 Dimethicone GRANSIL PC-12®
INCI: Isododecane (and) Polysilicone-11 (and) Glyceryl Laurate (and) Cetyl PEG/PPG 10/1 Dimethicone (and) PEG-10 Dimethicone GRANSIL WO-II®
INCI: Cyclopentasiloxane (and) Polysilicone-11 (and) Glyceryl Laurate (and) Cetyl PEG/PPG 10/1 Dimethicone (and) PEG/PPG-18/19 Dimethicone Particularly preferred polysilicon-11 used in the composition according to the present invention, are
GRANSIL DMCM-5® (INCI NAME DIMETHICONE (AND) CYCLOPENTASILOXANE (AND) POLYSILICON-11): gel consisting of polysilicone-11, a low viscosity dimethicone fluid (1-20 cst) and cyclomethicone, and
GRANSIL WO® (INCI NAME CYCLOPENTASILOXANE (AND) POLYSILICON-11 (AND) GLYCERYL LAURATE (AND) CETYL PEG/PPG 10/1 DIMETHICONE (AND) PEG/PPG-18/18 DIMETHICONE) composed of cyclopentasiloxane, polysilicone-11, glyceryl laurate, Cetyl PEG/PPG-10/1 dimethicone and PEG/PPG-18/18 dimethicone.

GRANSIL DMID®
INCI: Dimethicone (and) Isododecane (and) Polysilicone-11

GRANSIL PC-12-WO®
INCI: Isododecane (and) Polysilicone-11 (and) Glyceryl Laurate (and) Cetyl PEG/PPG 10/1 Dimethicone (and) PEG-10 Dimethicone Solid Particles Having an Optical Effect:

The emulsions of the invention preferably comprise more than 0.5 wt % of solid particles having at least one optical effect.

Preferably the weight ratio of the solid particles to the polysilicone-11 is comprised between 1 and 2 and, preferably, between 1 and 1.5. The emulsions of the invention are found to have the most satisfactory physical properties (ease of spreading, soft non-drying and non-greasy feeling on the skin) when the weight ratios are in these ranges.

The emulsions of the invention comprise more than 0.5 wt % of solid particles having at least one optical effect, preferably in proportions ranging from 0.5 wt % to 20 wt % by weight, and more preferably from 1 to 15 wt % by weight, for example from 2 to 12 wt % by weight, more precisely from 3 to 10 wt % by weight, and preferably from 3 wt % to 7 wt % by weight of the total weight of the composition.

For the purpose of this invention solid particles are defined as particles being intrinsically insoluble in the emulsion including encapsulated materials that otherwise would be soluble in the emulsion.

In the present invention solid particles having an optical effect, in very general terms, may be considered as those particles which when applied to the skin, in a cosmetic composition, modify the direction or intensity of transmitted, reflected or diffused light on or from the skin. Thus the solid particles having an optical effect, as defined in the current invention, may be divided into the following categories (a) particles that absorb visible light, thus producing a color effect, that is, pigments and pearls (b) particles having high diffuse reflectance, low specular reflectance and high diffuse transmittance, that is soft-focus particles (c) particles which reduce the shininess (increase the matt aspect the skin) by absorbing sebum, that are mattifying powders (d) particles which change the chromaticness of reflected light. Chromaticness corresponds to the hue and saturation of a colour. The higher the chromaticness the more saturated is the colour. Particles exhibiting this property enhance the apparent edge shape of a structure thus produce a sculpting or "morphing" or effect. (e) Particles that absorb the UV rays are also included in the definition of particles with an optical effect, thus solid UV sunscreens. (f) Particles that have high refractive index which yield optical effects, such as silicone elastomers.

(a) Pigments and Pearl Particles

Suitable pigments include inorganic or organic pigments. Organic pigments generally consist of insoluble metallic salts of certified color additives, referred to as the Lakes. Inorganic pigments include iron oxides such as red, black, yellow and the like; ultramarines, chromium, chromium hydroxide colors, and mixtures thereof. Particular examples of pigments include titanium dioxide, D&C Red #6 Barium Lake, D&C Red #7 Calcium Lake, D&C Red #34 Calcium Lake, FD&C Yellow #Aluminum Lake, Ferric Ferrocyanide, Red lion Oxide, Black Iron Oxide, Mica, Bismuth Oxychloride, Guanine.

Interferential pigments are also mentioned as solid particles having at least one optical effect. The term "interference pigment" denotes a pigment capable of producing a colour via an interference phenomenon, for example between the light reflected by a plurality of superposed layers with different refractive indices, especially a succession of layers with high and low refractive indices. An interference pigment may, for example, comprise more than four layers with different refractive indices. The layers of the interference pigment may or may not surround a core, which may or may not have a flattened shape. Pearls are examples of interference pigments.

Examples of pearls, also known as nacres that may be mentioned include nacreous pigments such as titanium mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superposed at least two successive layers of metal oxides and/or of organic dyestuffs.

Pigments and pearls used in the composition of the invention may be platelet-shaped, spherical, elongated or needle-shaped, or irregularly shaped, porous or non-porous, charged or uncharged. It is well known by those skilled in the art that they may be surface coated or uncoated with a variety of processes to improve, alter, or modify their surface properties.

(b) Soft Focus Particles

It is known that powders with high diffuse reflectance, low specular reflectance and high diffuse transmittance otherwise known as soft-focus powders or blurring agents give the skin a smoother appearance, by reducing the difference in luminosity between the valley and the edges of wrinkles and imperfections.

Examples of powders having a soft focus effect include powders of natural or synthetic origin such as mica, titanated mica, alumina, aluminum silicate, silica, fumed silica, silica silylate, titanium dioxide and serecite, composite talc/titanium dioxide/alumina/silica powders, such as those sold under the trade name COVERLEAF AR-80™ by Catalyst & Chemicals, Japan.

Non-mineral powders with a soft focus effect include polyamide, (for example NYLON®powders, such as, for example, the NYLON® 12 particles of the Orgasol type from Atofina, with a mean size of 10 microns, poly(methyl(meth) acrylate) such as, for example, the hollow PMMA spheres sold under the name COVABEAD LH85™ by Wacker, as well as and other acrylate copolymers polyethylene, silk powder, polyurethane, hexyldecyldiisocyanate trimethylol hexyllactone crosspolymer and silica, micronized teflon (PTFE), boron nitride.

Many soft focus powders are composites of mineral and non-mineral components. For example, the URETENDER V® range distributed by SACI CFPA, are composed of mica, titanium dioxide and polyurethane.

(c) Skin Mattifying Particles

Skin mattifying powders are used mainly to reduce the shininess of skin by adsorbing sebum and the excess oil of the composition not adsorbed by the skin.

Examples of mattifying powders can be soft focus powders as mentioned above which also act as mattifying agents, for example talc, starch, mica, silica which may or may not be coated, nylon powders, PTFE, polyethylene powders, poly-beta-alanine or poly(methyl) (meth)acrylate powders. All have the capacity to absorb excess sebum. One can also mention vinylpyrrolidone/1-triacontene copolymers (US2002182158), styrene-acrylic (EP1103245) or melamine-formaldehyde or urea-formaldehyde (U.S. Pat. No. 6,284,281) resin particles as examples of mattifying powders.

(d) Sculpting or "Morphing" Particles

"Morphing" particles are those which give rise to a sculpting effect when applied to a structured feature in particular the face. Specifically, these materials enhance the visible contrast between the areas of the face in light and in shadow thus rendering the face more "sculpted".

These materials may be simple inorganic compound such as titanium dioxide in a flaky form (for example TF-17-E® from Isihara, Japan), or may be composite powders with a mineral substrate layer, for example, mica or silica. Recently, optically anisotropic materials derived from organic polymers coated with colorants have been have been promoted for their morphing properties. 3D-TECH® from Daito Kasei, Japan, is an example of this type of material. It is composed of hemi-spheres of PMMA coated with organic colors displaying this morphing effect.

Similarly any of these "morphing" particles mentioned above may be coated with a hydrophobic coating.

(e) Solid UV Filter Particles

For the purpose of this invention, solid UV filters are those UV absorbing agents which are not soluble in the emulsion. They may be organic or inorganic.

Inorganic UV filters may be included in the composition of the invention. They may be selected from pigments (average size of the primary particles: generally from 5 nm to 100 nm, preferably from 10 nm to 50 nm) of metal oxides that are coated or uncoated, such as, for example, pigments of titanium oxide (amorphous or crystallized in rutile and/or anatase form), of iron oxide, of zinc oxide, of zirconium oxide or of cerium oxide, or mixtures thereof. Conventional coating agents are, moreover, alumina and/or aluminum stearate. Examples of commercially available titanium dioxide are UV Cut TiO2® and UV Cut TiO2-40DM®, both commercialised by Grant Industries. These are dispersions of surface treated titanium dioxide having a primary particle size of 16 nm in cyclopentasiloxane and low viscosity (5 cSt) dimethicone, respectively.

(f) High Refractive Index Particles

Enhancement of the overall appearance of the skin by providing strong blurring effects to give anti-wrinkle/fine line effects, skin smoothness, and radiance while unifying color complexion can be achieved with materials having high intrinsic refractive index, preferably silicone elastomers different from polysilicone-11.

Examples of silicone elastomers that are not polysilicone-11 are organopolysiloxane cross-polymers (U.S. Pat. No. 4,980,167) having the general formula

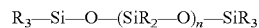

R being the same or different monovalent organic radicals such as alkyl or aryl groups. These molecules vary in terms of chemistry and degree of cross-linking thus giving rise to different physical characteristics, including swelling capability.

Examples are Alkyl Cetearyl Dimethicone Crosspolymer sold under the commercial name VELVESIL 125™ from Momentive Wilton, Conn., U.S.A., PEG-12™ Dimethicone Crosspolymer commercially available as Dow Corning 9011 from Dow Corning, dimethicone vinyl dimethicone crosspolymer commercially available as KSG-15™ from Shin-Etsu Silicone of America, Akron Ohio, U.S.A.

Furthermore, these elastomers may be in the form of a powder coated with silicone resin, for example, with silsesquioxane resin, as described, for example, in U.S. Pat. No. 5,538,793, the content of which is incorporated by way of reference.

Other elastomeric organopolysiloxanes in the form of spherical powders may be powders of hybrid silicone functionalized with fluoroalkyl groups, sold, for example, under the name KSP-200™ by the company Shin-Etsu and powders of hybrid silicones functionalized with phenyl groups, sold, for example, under the name KSP-300™ by the company Shin-Etsu.

Silicone-Based Emulsifiers:

The water-in-oil emulsion compositions typically comprises a silicone emulsifier in an amount of from about 0.25 wt % to about 7 wt %, more preferably in an amount of from about 0.5 wt % to about 3 wt %, even more preferably in an amount of from about 0.5 wt % to about 1.5 wt %, based on the weight of the emulsion composition.

The silicone-based emulsifiers of the invention include linear or branched silicones, which have emulsifying properties. In general, emulsifying properties are provided by modification with polyether groups. Furthermore, the silicones may be alkyl modified.

The silicone based emulsifiers may be crosslinked, thus consisting of polyether modified silicone elastomers.

Preferred silicone emulsifiers suitable for use in the present invention include those emulsifiers having the general formula (I):

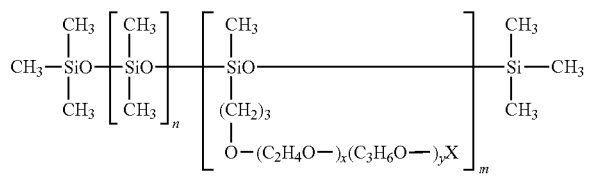

wherein X is selected from the group consisting of hydrogen, alkyl, alkoxy and acyl groups having from about 1 to about 16 carbon atoms,
n is from about 1 to about 100,
m is from about 1 to about 40,
x and y are independently from about 10 to about 2000.

Silicone emulsifiers which are suitable for use in the present compositions include, but are not limited to, dimethicone copolyols, cetyl dimethicone copolyols, laurylmethicone copolyols, including crosslinked forms thereof, and mixtures thereof.

The dimethicone copolyol is preferably an oxypropylenated and oxyethylenated polydimethylsiloxane. It can contain alkyl groups of more than 8 carbon atoms, especially C8-C22.

Dimethicone copolyols that may be used include those corresponding to formula (II) below:

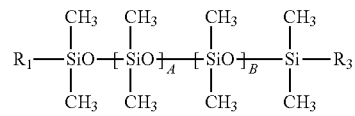

in which:
R1, R2 and R3, independently of each other, represent a C1-C6 alkyl radical or a radical —(CH2)x-(OCH2CH2)y-(OCH2CH2CH2)z, —OR4,
at least one radical R1, R2 or R3 not being an alkyl radical,
R4 being a hydrogen, a C1-C3 alkyl radical or a C2-C4 acyl radical
A is an integer ranging from 0 to 200;
B is an integer ranging from 0 to 50; with the condition that A and B are not simultaneously equal to 0;
x is an integer ranging from 1 to 6;
y is an integer ranging from 1 to 30; and
z is an integer ranging from 1 to 5.

According to one preferred embodiment of the invention, in the compound of formula (II), R1=R3=methyl radical, x is an integer ranging from 2 to 6 and y is an integer ranging from 4 to 30. R4 is in particular hydrogen.

The composition can contain at least one C8-C22 alkyl dimethicone copolyol. The C8-C22 alkyl dimethicone copolyol present in the composition according to the invention may be in particular an oxypropylenated and oxyethylenated polymethyl (C8-C22)alkyl dimethyl methyl siloxane.

The C8-C22 alkyl dimethicone copolyol is advantageously a compound of formula (III) below:

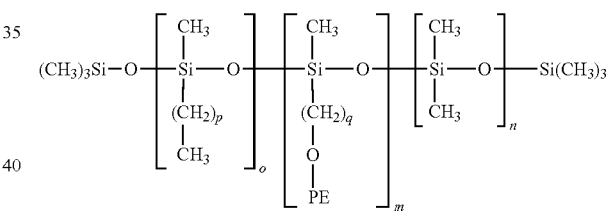

in which:
PE represents (—C2H4O)x—(C3H6O)y—R, R being chosen from a hydrogen atom and an alkyl radical containing from 1 to 4 carbon atoms, x ranging from 1 to 100 and y ranging from 1 to 80;
m ranging from 1 to 40;
n ranging from 10 to 200;
o ranging from 1 to 100;
p ranging from 7 to 21; and
q ranging from 0 to 4.

In particular, R=H; m=1 to 10; n=10 to 100; o=1 to 30; p=15; and q=3.

C8-C22 alkyl dimethicone copolyols that may be mentioned include cetyl dimethicone copolyol, for instance the product sold under the name ABIL EM-90™ by the company Goldschmidt.

Specific examples of preferred silicone emulsifiers include, but are not limited to:
  dimethicone copolyols such as DC5225C™, DC3225C™ and DC 5000™ (commercially available from Dow Corning Corp.) having as an INCI name PEG/PPG-18/18 dimethicone;
  SF1228™, SF1328™ and SF1528™ (commercially available from General Electric Co.);

SILWET L-7602™ and SILWET L-7622™ (commercially available from CKWitco);

cetyl dimethicone copolyols such as ABIL WE-09™ (INCI name cetyl dimethicone polyglyceryl-4-isostearate (and) cetyl dimethicone copolyol (and) hexyl laurate), ABIL WS08™ and ABIL EM 90™ (INCI name cetyl PEG/PPG-10/1 dimethicone) all commercially available from Goldsmith;

octyldimethicone ethoxyglucoside copolyols such as BELSIL SPG 128 VP™ (commercially available from Wacker);

dimethicone copolyol crosspolymers such as KGS21™ (commercially available from Shin Etsu); and laurylmethicone copolyols such as DC 5200™ commercially available from Dow Corning Corp.

The silicone emulsifier may be present as a preblend with polysilicon-11, as in GRANSIL WO® which is composed of cyclopentasiloxane, polysilicone-11, glyceryl laurate, Cetyl PEG/PPG-10/1 dimethicone, PEG/PPG-18/18 dimethicone.

Stabilizer Agents:

Although not compulsory, the compositions of the invention may also contain stabilizer agents such as gelling agents, electrolytes, or thickeners.

Gelling agents can be chosen from modified or unmodified carboxyvinyl polymers, polyacrylamides, modified or unmodified clays, polysaccharide biopolymers, alginates, modified or unmodified celluloses, and mixtures thereof.

The gelling agent may be a copolymer of 2-acrylamido 2-methylpropanesulfonic acid (AMPS) with at least one other comonomer. The AMPS monomer may be in a free form or in a neutralized or partially neutralized form The comonomer may be hydrophobic or not. It may be chosen from the group consisting of ethylenically unsaturated monomers bearing at least one hydrophobic moiety.

Such comonomers may be chosen from acrylates and acrylamides of Formula IV:

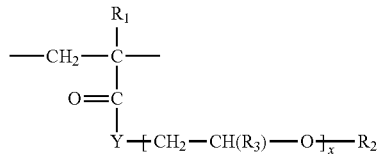

Formula IV wherein:

$R_1$ and $R_3$, identical or different, are a hydrogen atom or a linear $C_1$-$C_6$ alkyl radical or a branched $C_3$-$C_6$ alkyl radical;

Y is O or NH;

$R_2$ is a hydrocarbon radical comprising from 6 to 50 carbon atoms;

x is a number from 0 to 100.

According to a preferred embodiment of this invention, $R_1$ is a methyl group. Preferably also, $R_2$ is a linear, branched or cyclic alkyl radical preferably comprising from 6 to 30 carbon atoms and more preferably from 12 to 22 carbon atoms, such as a n-dodecyl or a n-behenyl radical. $R_3$ is preferably H, so the comonomer comprises at least one oxyethylene chain. As an alternative, $R_3$ may be a methyl group, so the comonomer comprises at least one oxypropylene chain. Moreover, x is preferably at least 1 and may range from 3 to 100, preferably from 3 to 50 and more preferably from 7 to 25. Most preferably, x is 25. In a preferred embodiment, y is NH.

Other copolymers include copolymers of AMPS with at least one water-soluble comonomer as described in US 2006/0239942, the content of which is incorporated herein by reference. Examples of such comonomers are (meth)acrylamide, maleic anhydride, N-vinyllactams such as N-vinylpyrrolidone, vinyl alcohol and (hydroxy)$C_1$-$C_6$-alkyl(meth)acrylates. Example of such a copolymer has the following INCI Name: Ammonium Acryloyldimethyltaurate/VP Copolymer.

In any case, the resulting copolymers may be cross-linked or non-cross-linked. They are preferably cross-linked.

The stabilizers agents included in the composition according to the present invention can be chosen from gelling agents as described above, electrolytes, polyols and hydrocolloids. Examples of polyols include glycerin, diglycerin, triglycerin, polyglycerin, polyethylene glycol and sorbitol.

Stabilizers are preferably present in a low amount such as 0.01 to 5 wt %, more preferably from 0.05 to 3 wt %, more preferably from 0.1 to 1 wt % based on the weight of the composition.

Additional Components:

The present compositions may further include non-silicone emulsifiers, preferably emulsifiers which would act as co-emulsifiers.

The non-silicon based emulsifiers that may be included may be non-ionic, anionic, cationic or amphoteric, and, in particular, esters of fatty acids and polyols, such as esters of fatty acids and glycerol, for example glyceryl laurate, esters of fatty acids and sorbitan, esters of fatty acids and polyethylene glycol; esters of fatty acids and sucrose; ethers of fatty alcohols and polyethylene glycol; alkylpolyglucosides; betaine and its derivatives; polyquaterniums; sulphate salts of ethoxylated fatty alcohols; sulfosuccinates; sarcosinates; alkyl- and dialkylphosphates and their salts; and soaps of fatty acids.

The compositions of the invention may contain film formers, i.e. those molecules commonly known in the art of cosmetics as having film forming properties. These are molecules, often synthetic or naturally occurring polymers that are capable of forming continuous films that adhere to skin or lips, alone or in the presence of an auxiliary film-forming agent. Examples of film formers that may be used in the compositions include acrylic polymers, polyurethanes, polyesters, polyamides, polyureas, and cellulosic polymers. Film formers may be present at a concentration of 0.05-5 wt % based on the total weight of the cosmetic composition.

Compositions of the present invention may also contain a skin conditioning agent (such as a humectant, exfoliant or emollient). Examples of such agents include *Butyrospermum parkii* (otherwise known as Shea butter), hyaluronic acid, sodium lactate, mannitol, amino acids, vitamins, urea, petroleum jelly and mixtures thereof. These agents are present in the compositions of the present invention in amounts generally ranging from about 0.1 wt % to about 10 wt %, based on the total weight of the cosmetic composition.

Preservatives and anti-oxidants that are commonly used in cosmetology as well as fragrances may also be used in the compositions of the invention. Examples of antioxidants are ascorbic acid and its derivatives, including ascorbyl palmitate, ascorbyl tetraisopalmitate, ascorbyl glucoside, magnesium ascorbyl phosphate, sodium ascorbyl phosphate and ascorbyl sorbate; tocopherol and its derivatives, such as tocopheryl acetate, tocopheryl sorbate and other esters of tocopherol; BHT and BHA.

Examples of such additives and others are cited in particular in the CTFA Dictionary (International Cosmetic Ingredient Dictionary and Handbook published by the Cosmetic, Toiletry and Fragrance Association, 10th Edition, 2004).

Active Ingredients:

One or more active ingredients may be present in the compositions of the invention at a concentration of 0.001-10 wt % weight of the total composition. Anti aging agents that may be included in the composition of the invention include acyl aminoacids (for example MAXILIP®, MATRIXYL 3000® OR BIOPEPTIDE CL® from SEDERMA or SEPILIFT® from SEPPIC), *Pisum sativum* extracts, hydrolyzed soy proteins, methylsilanol derivatives such as methylsilanol mannuronate, hydrolyzed *cucurbita* pepo seedcake, and Scenedesmus extract.

Anti-pollution agents such as Moring a pterygosperma seed extracts may also be included.

Keratolytic agents, such as α-hydroxyacids (for instance, glycolic, lactic, citric, malic, mandelic or tartaric acid) and (β-hydroxyacids (for instance, salicylic acid), and their esters, including $C_{12-13}$ alkyl lactate, and plant extracts containing these hydroxyacids, such as *Hibiscus sabdriffa* extracts may also be included.

Anti-inflammatory agents, such as bisabolol, allantoin, tranexamic acid, zinc oxide, sulfur oxide and its derivatives, chondroitin sulfate, glycyrrhizinic acid and its derivatives such as glycyrrhizinates and their mixtures may be included in the compositions of the invention.

The emulsions of the invention are suitable for use for making up the face and/or lips or eyelids, preferably as foundations. They may also be used as a base for make-up, or as a skin care cream to be applied on the body or face. They may be in the form of a liquid, cream, gel or semi-solid.

The emulsions of the invention may also be applied to the skin and/or lips for protecting the skin and/or lips against UV damage.

The water-in-oil composition preferably contains low water content, preferably between 10 and 40 wt %, more preferably 10 and 30 wt %, for example between 20 and 25 wt % based on the weight of the composition.

Method for the Preparation of the Compositions:

The invention also provides a general method for the preparation of the compositions described above.

According to the process for preparing the emulsion described above, the following step can be performed in that order or in another order:

1—Dispersion of the Polysilicone-11 in an hydrophobic solvent to form a gel,
2—Addition of the silicon emulsifier to the previous gel, and mixture with a water phase,
3—Addition of the solid particles providing at least one optical effect.

According to the first step, polysilicone-11 may already be provided in the solvent (for example in GRANSIL DMCM-5® the vehicle is cyclomethicone, in GRANSIL PC-12® the vehicle is isododecane). If it is not, then the polysilicone-11 should be pre-dispersed in a solvent and then combined with the silicone emulsifier.

In two preferred embodiments the silicone emulsifier and a portion of the polysilicone-11 are provided as a pre-dispersion commercially available under the tradenames GRANSIL WOO and GRANSIL PC12 WO®.

The rest of the polysilicone-11 may be added in step (1) or at a later stage in the process. In a second step (2) the aqueous phase is formed in a separate container and then added to the polysilicone-11 mixture of the previous step.

Before the third step (3) oil components such as emollients, preservatives and/or perfumes can be combined and then added to the polysilicone 11 mixture.

Active ingredients are added to either the aqueous phase or the oil components according to their hydrophobicity/hydrophilicity.

According to step (3), solid particles having an optical effect are added to the rest of the composition. The addition of the particles can be carried out in a number of ways at different steps in the process; they may be added directly to the polysilicone-11 during step (1), either before or after the addition of the silicone emulsifier. They may be added directly to the aqueous phase in step (2). Alternatively, the solid particles with an optical effect may be pre-dispersed, in either a portion or all of the polysilicone-11 and this pre-dispersion is then added to the mixture either during step (1) or in a fourth step.

If the solid particles are added directly to the composition, rather than as a pre-dispersion in polysilicone-11, it is preferred that the total amount of the polysilicone-11 in the formulation is present before the solid particles are added. Otherwise the emulsion may not be stable and phase separation may occur.

In a preferred embodiment a sub-portion of the total polysilicone-11 is added in step (1), and then, step (2) and (3) are carried out as outlined above. The pigments are pre-dispersed in the remaining portion of polysilicone-11 and in a fourth step this pre-dispersion is added to the main mixture. In general, preservatives are added in the last step.

Method for Making Up the Face

Making up the skin is the process generally understood to comprise applying a make-up composition to the skin and/or so as to hide skin imperfections, unify the color complexion, reduce the appearance of skin discoloration and wrinkles and, if necessary, reduce the shiny appearance of oily skin. The present invention includes a process for making up skin and/or lips and/or for protecting the skin against UV damage, comprising topically applying the emulsion onto skin and/or lips.

The compositions of the present invention may be applied by hand. Alternatively, or in conjunction therewith, they may be applied via an applicator such as sponges, cotton, brushes and puffs of natural or synthetic materials. In addition, the applicator may be attached to a container, said container serving as a reservoir for the cosmetic composition. The container that serves as reservoir for the cosmetic composition may be disposed with a pump or spray or other mechanism for dispensing the composition.

As stated in the introduction one of the inconveniences of most make-up compositions is that after a number of hours after application on the skin they may start to look and/or feel dry. In general, one has to completely remove and re-apply the make-up to achieve a "freshly applied" look and feel on the skin. Surprising, it has been found that the emulsions of the present invention once applied to the skin can easily absorb further amounts of water or non-silicon oil which is applied as a second composition on top the previously applied emulsion layer. Thus, an emulsion of the invention, for example, a make-up, may be freshened by applying and mechanically blending in a further amount of water or aqueous composition, or non-silicon oil or a non-silicon containing oil-based composition.

This second composition for refreshing the emulsions of the invention may be in the form of a liquid, gel or cream. It may be applied to the skin directly using the fingers or using an applicator or using a spray, spritz, pump or other dispensing apparatus. In a preferred embodiment the second composition is an aqueous solution applied to the skin using a spray apparatus.

The second composition may contain any of the preservatives and/or active agents, listed in the previous paragraphs. The active ingredient or ingredients may be present in a range of 0.001-10% weight of the total composition. In a preferred embodiment the second composition for refreshing the make-up is an aqueous solution containing approximately 1.25% malachite extract. Malachite has been traditionally known for its anti-oxidant activity.

After application to the skin the second composition is mechanically blended into the previously applied emulsion composition already present on the skin. The mechanical blending may be carried out using the fingers by patting or gently rubbing, or by using an applicator such as a sponge, cotton pad, or puff of natural or synthetic material. Thus, a make-up which is applied on the skin, for example in the morning, can be refreshed, for example, 2-12 hours later, by applying the second composition, for example, an aqueous solution, and then by blending the applied second composition into the make-up layer. The make-up is refreshed and appears as if it has been freshly applied. The color remains true and no streaking occurs.

Kit-of-Parts:

The invention provides a kit-of-parts comprising two containers. The first container serves as a reservoir for the make-up composition which comprises an emulsion of the invention and can have a form as described in the previous paragraphs. The second serves as a reservoir for the second composition used to refresh the make-up. The second container may have attached a mechanism for spraying or otherwise dispensing the composition. The two containers may be two separate entities not attached to each other, or may be partially or fully attached to each other. Thus, the kit may be in the form of at least two sub-containers or sub-compartments which hold separately the first and second composition, these sub compartments either being physically joined together or being held within a separate main container.

EXAMPLES

The compositions described in Example 1 were tested for stability and example 1A was tested for sensorial performance (see Example 2). Example 3 is a comparative stability study of emulsions that are not of part of the invention.

Not only are the compositions of the invention stable but they have surprisingly and totally unexpected superior sensorial properties as confirmed by the results of example 3 below, where the preferred execution of the invention, Example 1, was evaluated against large population of commercial products and conventional make-up products by a panel made of 20 sensorial experts.

The following compounds could be prepared in a manner which is conventional for the skilled person. The quantities indicated below are expressed as percentages by weight.

Example 1

Cosmetic Compositions

Example 1A

Foundation Make-Up

| Ingredients | Percentage |
| --- | --- |
| Seq 1 | |
| GRANSIL WO ® | 35.0 |
| CYCLOPENTASILOXANE (AND) | |
| POLYSILICONE-11 (AND) GLYCERYL LAURATE | |

-continued

| Ingredients | Percentage |
| --- | --- |
| (AND) CETYL PEG/PPG 10/1 DIMETHICONE | |
| (AND) PEG/PPG-18/18 DIMETHICONE | |
| Seq 2 | |
| Gelling agent | 0.3 |
| Ammonium Acryloyldimethyltaurate/ | |
| VP Copolymer | |
| Hydrating agent | 1 |
| Deionized water | q.s.p. 100% |
| Seq 3 | |
| Oil | 4 |
| Preservative | 1 |
| Fragrance | 0.3 |
| Seq 4 | |
| GRANSIL DMCM-5 ® | 28.0 |
| DIMETHICONE (AND) CYCLOPENTASILOXANE | |
| (AND) POLYSILICONE-11 | |
| Titanium Dioxide | 5.0 |
| Yellow iron oxide | 1.5 |
| Red Iron Oxide | 0.5 |
| Black Iron Oxide | 0.2 |

To prepare the above composition, Seq. 1 is put in a vessel at 25° C. Prepare Seq 2 ingredients in a separate vessel and mix until uniform. Then add Seq 2 to Seq 1 using propeller type mixing and mix until uniform. Prepare Seq 3 in a separate vessel and mix until uniform. Then add Seq 3 to Seq 1 and 2 using propeller type mixing. Prepare Seq 4 in a separate vessel and mix until uniform. Finally add Seq 4 to the previous prepared mixture. Mix with propeller type mixing until uniform.

The emulsion is stable: the particles remain well dispersed and there is no phase separation observed after storage at 20° C. for 1 month. In addition, unique sensorial qualities are obtained.

Example 1B

Foundation Make-Up

| Ingredients | Percentage |
| --- | --- |
| Seq 1 | |
| GRANSIL PC-12-WO ® | 35.0 |
| ISODODECANE (AND) POLYSILICONE-11 (AND) | |
| GLYCERYL LAURATE (AND) CETYL PEG/PPG | |
| 10/1 DIMETHICONE (AND) PEG-10 DIMETHICONE | |
| GRANSIL ® UV Cut Titanium Dioxide DM | 12.5% |
| TITANIUM DIOXIDE (AND) DIMETHICONE (AND) | |
| HEXYL LAURATE (AND) PEG-10 DIMEHTICONE | |
| (AND) POLYGLCERYL-4 ISOSTEARATE | |
| (AND) STEARIC ACID (AND) ALUMINA | |
| Seq 2 | |
| Gelling agent | 0.2 |
| Ammonium Acryloyldimethyltaurate/ | |
| VP Copolymer | |
| Hydrating agent | 1 |
| Deionized water | q.s.p. 100% |
| Seq 3 | |
| Organic Sunscreen | 5.0 |
| Preservative | 1 |
| Fragrance | 0.3 |

-continued

| Ingredients | Percentage |
|---|---|
| Seq 4 | |
| GRANSIL DMID ® ISODODECANE (AND) DIMETHICONE (AND) POLYSILICONE-11 | 28.0 |
| Titanium Dioxide | 5.0 |
| Yellow iron oxide | 1.5 |
| Red Iron Oxide | 0.5 |
| Black Iron Oxide | 0.2 |

To prepare the above composition, Seq. 1 is put in a vessel at 25° C. Prepare Seq 2 ingredients in a separate vessel and mix until uniform. Then add Seq 2 to Seq 1 using propeller type mixing and mix until uniform. Prepare Seq 3 in a separate vessel and mix until uniform. Then add Seq 3 to Seq 1 and 2 using propeller type mixing. Prepare Seq 4 in a separate vessel and mix until uniform. Finally add Seq 4 to the previous prepared mixture. Mix with propeller type mixing until uniform.

The emulsion is stable: the particles remain well dispersed and there is no phase separation observed after storage at 20° C. for 1 month.

Example 1C

Foundation Make-Up

| Ingredients | Percentage |
|---|---|
| Seq 1 | |
| GRANSIL PC-12-WO ® ISODODECANE (AND) POLYSILICONE-11 (AND) GLYCERYL LAURATE (AND) CETYL PEG/PPG 10/1 DIMETHICONE (AND) PEG-10 DIMETHICONE | 35.0 |
| GRANSIL ® UV Cut Titanium Dioxide DM TITANIUM DIOXIDE (AND) DIMETHICONE (AND) HEXYL LAURATE (AND) PEG-10 DIMEHTICONE (AND) POLYGLCERYL-4 ISOSTEARATE (AND) STEARIC ACID (AND) ALUMINA | 12.5% |
| Seq 2 | |
| Gelling agent Ammonium Acryloyldimethyltaurate/ VP Copolymer | 0.2 |
| Hydrating agent | 1 |
| Deionized water | q.s.p. 100% |
| Seq 3 | |
| Oil | 5.0 |
| Preservative | 1 |
| Fragrance | 0.3 |
| Seq 4 | |
| GRANSIL DMID ® ISODODECANE (AND) DIMETHICONE (AND) POLYSILICONE-11 | 28.0 |
| Titanium Dioxide | 5.0 |
| Yellow iron oxide | 1.5 |
| Red Iron Oxide | 0.5 |
| Black Iron Oxide | 0.2 |

To prepare the above composition, Seq. 1 is put in a vessel at 25° C. Prepare Seq 2 ingredients in a separate vessel and mix until uniform. Then add Seq 2 to Seq 1 using propeller type mixing and mix until uniform. Prepare Seq 3 in a separate vessel and mix until uniform. Then add Seq 3 to Seq 1 and 2 using propeller type mixing. Prepare Seq 4 in a separate vessel and mix until uniform. Finally add Seq 4 to the previous prepared mixture. Mix with propeller type mixing until uniform.

The emulsion is stable: the particles remain well dispersed and there is no phase separation observed after storage at 20° C. for 1 month.

Example 1D

Foundation Make-Up

| Ingredients | Percentage |
|---|---|
| Seq 1 | |
| GRANSIL PC-12-WO ® ISODODECANE (AND) POLYSILICONE-11 (AND) GLYCERYL LAURATE (AND) CETYL PEG/PPG 10/1 DIMETHICONE (AND) PEG-10 DIMETHICONE | 35.0 |
| GRANSIL ® UV Cut Titanium Dioxide DM TITANIUM DIOXIDE (AND) DIMETHICONE (AND) HEXYL LAURATE (AND) PEG-10 DIMEHTICONE (AND) POLYGLCERYL-4 ISOSTEARATE (AND) STEARIC ACID (AND) ALUMINA | 12.5% |
| Seq 2 | |
| Gelling agent Ammonium Acryloyldimethyltaurate/ VP Copolymer | 0.2 |
| Hydrating agent | 1 |
| Deionized water | q.s.p. 100% |
| Seq 3 | |
| Organic Sunscreen | 5.0 |
| Preservative | 1 |
| Fragrance | 0.3 |
| Seq 4 | |
| GRANSIL ININ ® ISONONYL ISONONANOATE (AND) POLYSILICONE-11 | 28.0 |
| Titanium Dioxide | 5.0 |
| Yellow iron oxide | 1.5 |
| Red Iron Oxide | 0.5 |
| Black Iron Oxide | 0.2 |

To prepare the above composition, Seq. 1 is put in a vessel at 25° C. Prepare Seq 2 ingredients in a separate vessel and mix until uniform. Then add Seq 2 to Seq 1 using propeller type mixing and mix until uniform. Prepare Seq 3 in a separate vessel and mix until uniform. Then add Seq 3 to Seq 1 and 2 using propeller type mixing. Prepare Seq 4 in a separate vessel and mix until uniform. Finally add Seq 4 to the previous prepared mixture. Mix with propeller type mixing until uniform.

The emulsion is stable: the particles remain well dispersed and there is no phase separation observed after storage at 20° C. for 1 month.

Example 1E

Foundation Make-Up

| Ingredients | Percentage |
|---|---|
| Seq 1 | |
| GRANSIL PC-12-WO ® ISODODECANE (AND) POLYSILICONE-11 (AND) | 35.0 |

-continued

| Ingredients | Percentage |
|---|---|
| GLYCERYL LAURATE (AND) CETYL PEG/PPG 10/1 DIMETHICONE (AND) PEG-10 DIMETHICONE | |
| GRANSIL ® UV Cut Titanium Dioxide DM | 12.5% |
| TITANIUM DIOXIDE (AND) DIMETHICONE (AND) HEXYL LAURATE (AND) PEG-10 DIMEHTICONE (AND) POLYGLCERYL-4 ISOSTEARATE (AND) STEARIC ACID (AND) ALUMINA | |
| Seq 2 | |
| Gelling agent | 0.2 |
| Ammonium Acryloyldimethyltaurate/ VP Copolymer | |
| Hydrating agent | 1 |
| Deionized water | q.s.p. 100% |
| Seq 3 | |
| Oil | 5.0 |
| Preservative | 1 |
| Fragrance | 0.3 |
| Seq 4 | |
| GRANSIL ININ ® | 28.0 |
| ISONONYL ISONONANOATE (AND) POLYSILICONE-11 | |
| Titanium Dioxide | 5.0 |
| Yellow iron oxide | 1.5 |
| Red Iron Oxide | 0.5 |
| Black Iron Oxide | 0.2 |

To prepare the above composition, Seq. 1 is put in a vessel at 25° C. Prepare Seq 2 ingredients in a separate vessel and mix until uniform. Then add Seq 2 to Seq 1 using propeller type mixing and mix until uniform. Prepare Seq 3 in a separate vessel and mix until uniform. Then add Seq 3 to Seq 1 and 2 using propeller type mixing. Prepare Seq 4 in a separate vessel and mix until uniform. Finally add Seq 4 to the previous prepared mixture. Mix with propeller type mixing until uniform.

The emulsion is stable: the particles remain well dispersed and there is no phase separation observed after storage at 20° C. for 1 month.

Example 1F

Make-Up Base

| Ingredients | Percentage |
|---|---|
| Seq 1 | |
| GRANSIL WO ® | 35.0 |
| CYCLOPENTASILOXANE (AND) POLYSILICONE-11 (AND) GLYCERYL LAURATE (AND) CETYL PEG/PPG 10/1 DIMETHICONE (AND) PEG/PPG-18/18 DIMETHICONE | |
| GRANSIL DMCM-5 ® | 20.5 |
| DIMETHICONE (AND) CYCLOPENTASILOXANE (AND) POLYSILICON-11 | |
| GRANSIL UV CUT TiO2 ® | 6.25 |
| TITANIUM DIOXIDE (AND) CYCLOPENTASILOXANE (AND) HEXYL LAURATE (AND) PEG-10 DIMETHICONE (AND) POLYGLYCERYL-4 ISOSTEARATE (AND) STEARIC ACID (AND) ALUMINA | |
| Seq 2 | |
| Gelling agent | 0.3 |
| Ammonium Acryloyldimethyltaurate/ VP Copolymer | |

-continued

| Ingredients | Percentage |
|---|---|
| Hydrating agent | 1 |
| Deionized water | q.s.p. 100% |
| Seq 3 | |
| Organic sunscreen | 7.5 |
| Preservative | 1 |
| Fragrance | 0.3 |

To prepare the above composition, Seq. 1 is put in a vessel at 25° C. Prepare Seq 2 ingredients in a separate vessel and mix until uniform. Then add Seq 2 to Seq 1 using propeller type mixing and mix until uniform. Prepare Seq 3 in a separate vessel and mix until uniform. Then add Seq 3 to Seq 1 and 2 using propeller type mixing.

The emulsion is stable: the particles remain well dispersed and there is no phase separation observed after storage at 20° C. for 1 month.

Example 2

Sensorial Tests

The foundation sensorial properties of Foundation Example 1A were tested according two different sensorial methods.

Sensorial Test 1:

The make-up composition of example 1A was subjected to sensorial evaluation by a panel of 20 testers using a standard method of sensory profile, QDA (registered trademark) quantitative descriptive analysis, as recommended by the professional guidelines: Guidelines for the Evaluation of the efficacy of cosmetic products, COLIPA GUIDELINES, second edition 2001. Collection of French standards AFNOR-DGC-CRF-1991—Quality control of food products —Sensory Analysis —ISBN 2-12-190843-9.—Sensory Analysis, European French standards, 6th edition, 2002—ISBN 2-12-190863-3.

The make-up composition of example 1A was applied with fingers to the hemi-face. Testers were asked to report on the feel and aspect of the make-up on initial application, as well as the make-up result.

Results:

Texture and Feel:

Initial application: Applied easily to the skin, soft texture.

Five minutes after application: Non-sticky (no effort required to release fingers after touching the skin three times), non-oily (no greasiness on the surface of the skin) with a powdery soft touch.

Make-Up Result:

Very even and natural result i.e. on application the make-up is distributed evenly over the entire application area, and the make-up is not detectable. It blends into the skin and does not give a mask-like effect.

Unifies the color complexion and skin looks smooth (wrinkles are slightly blurred). Skin is left with a slightly matte (non-shiny) and powdery finish.

TABLE 2

| Attribute | Value | Foundation of Example 1A | Reference 1 | Reference 2 |
|---|---|---|---|---|
| PRODUCT SOFTNESS | Mean | 6.8 | 5.7 | 6.3 |
| | SD (n-1) | 1.2 | 1.2 | 1.2 |

TABLE 2-continued

| Attribute | Value | Foundation of Example 1A | Reference 1 | Reference 2 |
|---|---|---|---|---|
| DRYING SPEED | Mean | 6.5 | 4.9 | 5.5 |
|  | SD (n-1) | 1.3 | 1.3 | 1.3 |
| COVERING EFFECT | Mean | 6.2 | 5.8 | 5.5 |
|  | SD (n-1) | 1.0 | 1.0 | 1.0 |
| UNIFYING (COLOR) | Mean | 6.2 | 5.4 | * |
|  | SD (n-1) | 0.7 | 0.7 | 0.7 |
| EVEN | Mean | 7.1 | 6.6 | 6.2 |
| CONSISTENCY | SD (n-1) | 0.7 | 0.7 | 0.7 |
| SMOOTHING | Mean | 6.6 | 5.8 | 5.3 |
| EFFECT | SD (n-1) | 0.6 | 0.6 | 0.6 |
| DETECTABLE | Mean | 2.7 | 3.2 | 4.3 |
| PRESENCE | SD (n-1) | 0.9 | 0.9 | 0.9 |
| RADIANCE | Mean | 6.4 | 5.8 | 5.1 |
|  | SD (n-1) | 0.8 | 0.8 | 0.8 |
| MATT FINISH | Mean | 6.4 | 6.1 | 6.2 |
|  | SD (n-1) | 1.0 | 1.0 | 1.0 |
| POWDERY FINISH | Mean | 5.0 | 3.3 | 4.1 |
|  | SD (n-1) | 1.6 | 1.6 | 1.6 |
| STICKINESS | Mean | 1.2 | 1.8 | 0.9 |
|  | SD (n-1) | 0.7 | 0.7 | 0.7 |
| SKIN SOFTNESS | Mean | 6.1 | 4.7 | 5.3 |
|  | SD (n-1) | 0.8 | 0.8 | 0.8 |

* not measured
Reference 1: PERFECT TOUCH ™ from Yves Saint Laurent
Reference 2: MULTIRéGéNéRANT-CLA ™ from Clarins Compared to the reference foundations, PERFECT TOUCH™ from Yves Saint Laurent and MULTIRÉGÉNÉRANT-CLA™ from Clarins which rank highly in aesthetic quality, and a large range of commercial products which have been studied using the same methodology, the foundations of the invention show a marked increase in radiance (6.4 compared to 5.8 and 5.1 for the references 1 and 2 respectively), in the unifying of the complexion (6.2 compared to 5.4 for the reference 1) and in smoothing effect (6.6 compared to 5.8 and 5.3 for references 1 and 2 respectively).

Sensorial Test 2:

Visual Evaluation in vivo of complexion radiance using the CLBT sensory method.

C. Musnier et al. Skin Research and Tech. 2004, 10, 50-56

Evaluation of the Radiance with the CLCT® method, in specific conditions of lighting: daylight+spots halogens

TABLE 3

| Attribute | Value | Make-up | SKIN without product | Make-up contri-bution | Signif. ANOVA (p) |
|---|---|---|---|---|---|
| LUMINOSITY | Mean | 5.8 | 5.5 | +0.3 | NS |
|  | Standard deviation (n-1) | 1.8 | 1.9 |  |  |
| UNIFYING EFFECT | Mean | 6.8 | 5.7 | +1.1 | 0.0002*** |
|  | Standard deviation (n-1) | 1.2 | 1.6 |  |  |
| PORE SIZE | Mean | 2.8 | 2.8 | 0 | NS |
|  | Standard deviation (n-1) | 1.6 | 1.8 |  |  |
| RED COMPLEXION | Mean | 2.1 | 2.4 | −0.3 | NS |
|  | Standard deviation (n-1) | 1.8 | 1.8 |  |  |
| SALLOW COMPLEXION | Mean | 1.3 | 2.0 | −0.7 | 0.0086** |
|  | Standard deviation (n-1) | 1.7 | 1.8 |  |  |

TABLE 3-continued

| Attribute | Value | Make-up | SKIN without product | Make-up contri-bution | Signif. ANOVA (p) |
|---|---|---|---|---|---|
| BEIGE COMPLEXION | Mean | 5.3 | 4.4 | +0.9 | 0.0084** |
|  | Standard deviation (n-1) | 2.6 | 2.6 |  |  |

**significant difference at 1% level
***significant difference at 0.1% level
NS: non-significant difference at 5% level The make-up product appears to be very smooth and very soft, reduces slightly the sallow aspect and increases the beige aspect. Thus the radiance of the skin is increased.

Smoothing, radiance, and softness are directly related to anti-aging benefits, for example, anti-wrinkle, unifying the complexion, masking imperfections and radiance associated with youthful skin. Typically a high coverage make-up is required to deliver these properties. Surprisingly, the inventive compositions deliver these anti-aging benefits without the need for a heavy make-up constituting a totally new sensorial/performance experience for the consumer.

Example 3

Comparative Compositions

To further illustrate the invention, the Examples below shows lack of stability when the content of Polysilicone-11 is reduced outside the range of the invention or is replaced by another silicone elastomer.

Comparative Example 3A

A similar composition as Example 1A was prepared, except that the concentration of polysilicone-11 was reduced from 6.7 wt % to 3.9 wt % wt. The difference was made up by adding cyclomethicone.

Compositions were formulated using the processing methods 1 and 2 described in example 1A. Both cases result in unstable emulsions, the pigments do not disperse and the emulsion separates.

Comparative Example 3B

The 6.7 wt % polysilicone-11 of composition 1A was replaced with 6.7 wt % of other silicone elastomers. For confirmation purposes, this percentage refers to the elastomer only and excludes the carrier/solvent.

Table 4 below shows the stability results obtained.

| Silicon Elastomer | Emulsion Stablility | Pigment Dispersion |
|---|---|---|
| Polysilicone-11 | Stable | Yes |
| VELVESIL ® 125[1] | Not stable | Yes |
| DOW CORNING ® 9011[2] | Not stable | No |
| GRANSIL ® EPSQ[3] | Not stable | No |

[1]C30-45 Alkyl Cetearyl Dimethicone Crosspolymer
[2]PEG-12 Dimethicone Crosspolymer
[3]Dimethicone/Divinyldimethicone/Silsesquioxane Crosspolymer It can be concluded from the above examples that only the composition containing Polysilicone-11 is stable compared to three other silicone elastomers tested in equivalent formulas. Only Polysilicone-11 results in a composition wherein the pigment remains dispersed and the emulsion remains stable.

Comparative Example 3C

The next Example illustrates the negative effect of replacing the silicone-based emulsifier with a conventional one.

| Ingredient | Percentage |
|---|---|
| Seq 1 | |
| Dimethicone | 14 |
| Cyclomethicone | 37 |
| Polysilicone-11 | 6.7 |
| Glyceryl Stearate | 1.3 |
| PEG-100 Stearate | 0.8 |
| Isohexadecane | 1 |
| Ammonium Polyacryloyldimethyltaurate | 1 |
| Seq 2 | |
| Gelling agent | 0.3 |
| Hydrating agent | 1 |
| Deionized water | q.s.p. 100% |
| Seq 3 | |
| Oil | 4 |
| Preservative | 1 |
| Fragrance | 0.3 |
| Seq 4 | |
| Titanium Dioxide | 5.0 |
| Yellow iron oxide | 1.5 |
| Red Iron Oxide | 0.5 |
| Black Iron Oxide | 0.2 |

To prepare the above composition, pre-mix Seq. 1 at 25° C. Prepare Seq 2 ingredients in a separate vessel. Mix until uniform. Then add Seq 2 to Seq 1 using propeller type mixing. Mix until uniform. Prepare Seq 3 in a separate vessel. Mix until uniform. Then add Seq 3 to Seq 1 and 2 using propeller type mixing. Finally add Seq 4. Mix with propeller type mixing until uniform.

The pigments do not disperse in the emulsion and the emulsion separates into the oil and water phases.

Furthermore, this illustrates that both the stability of the emulsions and their sensoriality are dependent upon the composition.

The invention claimed is:

1. A stable water-in-oil make-up emulsion comprising:
   (a) at least 5 wt. % polysilicone-11 silicone elastomer based on the total weight of the stable water-in-oil make-up emulsion, said polysilicone-11 being either dispersed or solubilized in a hydrophobic solvent to form a gel,
   (b) at least 0.5 wt. % of solid particles having an optical effect based on the total weight of the stable water-in-oil make-up emulsion, and
   (c) at least one silicone emulsifier, wherein one of said at least one silicone emulsifier is dimethicone copolyol comprising at least one oxyethylene group and at least one oxypropylene group.

2. The emulsion of claim 1, wherein the hydrophobic solvent comprises at least one volatile solvent.

3. The emulsion of claim 1, wherein the hydrophobic solvent is volatile.

4. The emulsion of claim 2, wherein the volatile hydrophobic solvent is selected from the group consisting of silicone oils, branched chain hydrocarbons, and mixture thereof.

5. The emulsion of claim 1, wherein polysilicone-11 is in the amount of about 6 wt % to about 30 wt %-of the total weight of the composition.

6. The emulsion of claim 1, wherein the weight ratio of the solid particles to the polysilicon-11 is comprised between 1 and 2.

7. The emulsion of claim 1, wherein the dimethicone copolyol is selected from the group consisting of cetyl PEG/PPG-10/1 dimethicone and PEG/PPG-18/18 dimethicone and mixtures thereof.

8. The emulsion of claim 1, wherein the solid particles are selected from the group consisting of pigments, pearls, lakes, powders, fillers, sunscreens and mixtures thereof.

9. The emulsion of claim 1, wherein the solid particles are in the amount from 0.5 wt % to 20 wt %.

10. The emulsion of claim 1, wherein the at least one silicone emulsifier is in the amount from 0.25 wt % to 7 wt %.

11. The emulsion of claim 1, further comprising ammonium acryloyldimethyltaurate/vp copolymer.

12. A process for preparing the emulsion of claim 1, comprising the following steps:
   dispersing the polysilicone-11 silicone elastomer in the hydrophobic solvent to form the gel;
   adding the silicone emulsifier to the gel, and mixing with a water phase; and
   adding the solid particles providing at least one optical effect.

13. The process according to claim 12 wherein the solid particles providing at least one optical effect are pre-dispersed in a portion of the polysilicone-11.

14. A make-up foundation including the emulsion of claim 1.

15. A process for making up skin or for protecting skin against UV damage, comprising topically applying the emulsion of claim 1 onto skin.

16. A kit comprising a first composition including the emulsion according to claim 1 and a second composition comprising a non-silicon continuous phase.

17. A method for applying make-up and refreshing the applied make-up to appear freshly applied to skin comprising the steps of:
   applying a first composition according to claim 1 to the skin;
   after an interval of time ranging from 2 to 12 hours applying a second composition onto the first composition; and
   blending the second composition into the first composition.

18. The method according to claim 17, wherein, the second composition is a composition selected from the group consisting of water, an aqueous composition, a non-silicon oil, and a non-silicon oil-based composition.

19. The method according to claim 17, wherein the second composition is blended into the first composition by patting or rubbing with the fingers.

* * * * *